(12) United States Patent
Eom (10) Patent No.: US 9,999,455 B2
(45) Date of Patent: Jun. 19, 2018

(54) SPINE FIXING APPARATUS

(71) Applicant: CORENTEC CO., LTD., Chungcheongnam-do (KR)

(72) Inventor: Yun-Seob Eom, Seoul (KR)

(73) Assignee: Corentec Co., LTD., Chungcheongnam-do (KR)

( * ) Notice: Subject to any disclaimer, the term of this patent is extended or adjusted under 35 U.S.C. 154(b) by 252 days.

(21) Appl. No.: 14/916,929

(22) PCT Filed: Jul. 9, 2015

(86) PCT No.: PCT/KR2015/007112
§ 371 (c)(1),
(2) Date: Mar. 4, 2016

(87) PCT Pub. No.: WO2016/024719
PCT Pub. Date: Feb. 18, 2016

(65) Prior Publication Data
US 2016/0206351 A1  Jul. 21, 2016

(30) Foreign Application Priority Data
Aug. 11, 2014 (KR) .......................... 10-2014-0103569

(51) Int. Cl.
*A61B 17/70* (2006.01)
*A61B 17/80* (2006.01)

(52) U.S. Cl.
CPC ...... *A61B 17/8033* (2013.01); *A61B 17/7059* (2013.01); *A61B 17/80* (2013.01);
(Continued)

(58) Field of Classification Search
CPC ............ A61B 17/7059; A61B 17/8033; A61B 17/8042
See application file for complete search history.

(56) References Cited

U.S. PATENT DOCUMENTS

| 2002/0065517 A1* | 5/2002 | Paul | ............... A61B 17/7059 606/279 |
| 2004/0019353 A1* | 1/2004 | Freid | ............... A61B 17/1728 606/915 |

(Continued)

FOREIGN PATENT DOCUMENTS

| KR | 10-2005-0032731 A | 4/2005 |
| KR | 10-2011-0021142 A | 3/2011 |

OTHER PUBLICATIONS

International Search Report dated Oct. 7, 2015, issued in PCT Application No. PCT/KR2015/007112, filed Jul. 9, 2015.
(Continued)

*Primary Examiner* — Christian Sevilla
(74) *Attorney, Agent, or Firm* — Workman Nydegger (57) ABSTRACT

A spine fixing apparatus including: a plate fixed to a spine; screws inserted into the spine by being coupled to the plate; a rotation member for rotary motion at a predetermined location between the screws; and sliding members provided at opposite sides of the rotation member and disposed between the rotation member and the screws. The rotation member can push the sliding members such that the sliding members rectilinearly move to cover upper surfaces of the screws. The spine fixing apparatus can facilitate the locking and unlocking of the screws by switching between lock and unlock modes, and can be firmly fixed to a spine. The plate has a window that enables an operator to identify a surgical region with naked eye. The window also allows the operator to easily bend the plate into a suitable shape for a patient's spine, and closely fix the plate to the spine.

13 Claims, 7 Drawing Sheets

(52) U.S. Cl.
CPC .......... *A61B 17/808* (2013.01); *A61B 17/809* (2013.01); *A61B 17/8042* (2013.01)

(56) References Cited

U.S. PATENT DOCUMENTS

2005/0075633 A1* 4/2005 Ross .................. A61B 17/7059
606/280
2009/0131988 A1 5/2009 Bush

OTHER PUBLICATIONS

Written Opinion dated Oct. 7, 2015, issued in PCT Application No. PCT/KR2015/007112, filed Jul. 9, 2015.

* cited by examiner

SPINE FIXING APPARATUS

TECHNICAL FIELD

The present invention generally relates to a spine fixing apparatus for fixing a spine. More particularly, the present invention relates to a spine fixing apparatus including: a plate fixed to a spine; screws inserted into the spine by being coupled to the plate; a rotation member for rotary motion at a predetermined location between the screws; and sliding members provided at opposite sides of the rotation member for rectilinear motion, each of the sliding members being disposed between the rotation member and each of the screws, wherein as the rotation member rotates, the sliding members are pushed such that the sliding members rectilinearly move to cover upper surfaces of the screws, whereby the spine fixing apparatus is capable of facilitating locking and unlocking of the screws by switching between lock and unlock modes, and is capable of being firmly fixed to a spine, wherein the plate is provided with a window formed therethrough with a predetermined surface area, thereby enabling an operator to identify the surgical region with his/her naked eye, thus facilitating a surgical procedure, and further enabling an operator to easily bend the plate into a suitable shape for a patient's spine, and closely fix the plate to the spine.

BACKGROUND ART

The human vertebral column consists of 32 to 35 vertebrae that form the spine of the body, and intervertebral discs that lie between adjacent vertebrae, wherein the vertebral column, i.e., the spine, forms the backbone of the trunk and communicates with the skull above and the pelvis below. The vertebrae include seven cervical vertebrae, twelve thoracic vertebrae, five lumbar vertebrae, five sacral vertebrae, and three to five coccygeal vertebrae, wherein in adults, the five sacral vertebrae are fused to form one sacrum, and the three to five coccygeal vertebrae are fused to form one coccyx.

In general, the cervical spine is at top of the vertebral column and consists of seven vertebrae, wherein the cervical spine includes, beginning from the top, the first cervical vertebra, also called as the atlas, which has a rounded-shaped articular surface supporting the skull but does not have a vertebral body nor a spinous process; the second cervical vertebra, also called as the axis, which helps cervical rotation and has the odontoid process that rises perpendicularly from the vertebral body; the third to the sixth cervical vertebrae have small and wide vertebral bodies, triangular shaped vertebral foramens, and the spinous processes that are divided into two at each end thereof, and the seventh cervical vertebra, also called as the vertebra prominens, which has the spinous process without divided ends.

The cervical spine having the structure and function described above may be deformed or damaged by external shock from an accident, or due to long term bad posture. A cervical plate (a cervical fixing apparatus) having a plate and a screw is used to fix a damaged or deformed cervical spine, wherein the cervical plate (the cervical fixing apparatus) is fixedly inserted into the cervical spine. However, the cervical plate (the cervical fixing apparatus) is problematic in that after surgical procedure, frequent motions in the cervical spine leads to a back-out problem, which means the screw that is fixedly inserted into the cervical spine falls out by being loosed.

As a document of a related art, Korean Patent Application Publication No. 10-2011-0021142 (Published Mar. 4, 2011) discloses "Cervical Fixing Apparatus".

To solve the back-out problem, the cervical fixing apparatus having a locking means has been proposed by the applicant of this invention. However, the cervical fixing apparatus is problematic in that the locking means accounts for most of the surface area of the plate, whereby it is difficult to bend the plate into a suitable shape for a patient's cervical spine during surgical procedure, and also makes it difficult to identify the surgical region within the plate with naked eye.

DISCLOSURE

Technical Problem

Accordingly, the present invention has been made keeping in mind the above problems occurring in the related art.

The present invention is intended to propose a spine fixing apparatus capable of easily switching between the lock mode and the unlock mode through simple mechanism by using screw holes, a rotation member for rotary motion at a predetermined location between the screw holes, and sliding members provided at opposite sides of the rotation member for rectilinear motion, thereby facilitating a surgical procedure.

The present invention is further intended to propose a spine fixing apparatus configured such that the sliding member is seated in an accommodation space of a plate, whereby even when the screw pushes up the sliding member in the lock mode, the sliding member is not separated from the plate, thereby being capable of firmly locking the screw.

The present invention is further intended to propose a spine fixing apparatus configured such that the rotation member is in a rhombic shape that has a major axis and a minor axis, thereby having smaller radius of gyration than that of rectangular shape. Thus, it is possible to reduce an overall size of the apparatus, thereby enabling the plate to be bent easily.

The present invention is further intended to propose a spine fixing apparatus configured such that in the lock mode, each end of the major axis of the rotation member supports a notch of a contact side, thereby stably supporting the sliding member. Thus, it is possible to limit the rectilinear motion of the sliding member efficiently.

The present invention is further intended to propose a spine fixing apparatus configured such that undesirable rotation caused by the external environment can be prevented by friction generated when a locking protrusion of the rotation member presses the plate; and in the lock mode, the locking protrusion is seated on a locking groove of the plate, thereby preventing rotation of the rotation member and stably supporting the sliding member. Thus, it is possible to increase the success rate of an operation.

The present invention is further intended to propose a spine fixing apparatus having a window formed through the plate, thereby facilitating a surgical procedure by securing a clear view of the surgical region.

The present invention is further intended to propose a spine fixing apparatus having a window in the plate, whereby it is easy to bend the plate corresponding to a cervical spine of a patient.

The objects of the present invention are not limited to those objects mentioned above, and other objects of the present invention will be understood by the following description, and more clearly understood by an embodiment of the present invention. Further, the objects of the present invention will be realized by methods in the claims and combinations thereof.

Technical Solution

In order to achieve the above object, according to one aspect of the present invention, there is provided a spine fixing apparatus, which has the following configuration.

The spine fixing apparatus according to an embodiment of the present invention includes: a plate fixed to a spine; screws inserted into the spine by being coupled to the plate; a rotation member for rotary motion at a predetermined location between the screws; and sliding members provided at opposite sides of the rotation member for rectilinear motion, each of the sliding members being disposed between the rotation member and each of the screws, wherein the spine fixing apparatus is capable of switching between a lock mode and an unlock mode.

In the spine fixing apparatus according to the embodiment of the present invention, the plate may include a plurality of screw holes for allowing the screws to be inserted thereinto, the screw holes being spaced apart from each other at predetermined intervals on the plate and formed through the plate; and the rotation member and the sliding members are disposed between a pair of the screw holes and have symmetrical structures based on the rotation member.

In the spine fixing apparatus according to the embodiment of the present invention, the plate may include an accommodation space formed by being depressed in a moving direction of the sliding members for accommodating the sliding members and the rotation member such that the sliding member rectilinearly moves within the accommodation space, switching between the lock mode and the unlock mode.

In the spine fixing apparatus according to the embodiment of the present invention, the accommodation space may include a first guide rail for guiding a motion of the sliding member by being configured to have a sliding surface so as to have a progressively narrower gap between opposed sides of the first guide rail with which the sliding members come into contact, as approaching from a lower surface of the accommodation space to an upper surface thereof, and a side wall of the sliding member comes into contact with the first guide rail, and includes a first sliding surface being in an inclined shape complementary to a shape of the first guide rail, wherein the first guide rail presses the first sliding surface so as to prevent the sliding member from being separated from the accommodation space.

In the spine fixing apparatus according to the embodiment of the present invention, the accommodation space may include a locking corner formed by being bent from a first end of the first guide rail to an inside of the accommodation space at almost right angle, the first end being oriented toward the screw hole, and a second guide rail being in an inclined shape in a same manner of the first guide rail by extending from the locking corner toward the screw hole in parallel with the first guide rail; and the side wall of the sliding member includes a side ridge formed by being bent from a first end of the first sliding surface to an inside of the sliding member at almost right angle, and a second sliding surface formed by being bent and extending from an end of the side ridge in parallel with the first sliding surface, and being in an inclined shape complementary to a shape of the second guide rail, wherein when switching to the lock mode, the side ridge is locked to the locking corner so as to limit the rectilinear motion of the sliding member, and the second guide rail presses the second sliding surface so as to prevent the sliding member from being separated from the accommodation space.

In the spine fixing apparatus according to the embodiment of the present invention, the accommodation space may include an insertion recession formed by being recessed from a second end of the first guide rail toward an outside of the accommodation space, the insertion recession being formed to have a width capable of receiving the first sliding surface of the sliding member, wherein after the sliding member is inserted into the accommodation space from an upper portion of the accommodation space in a state where the first sliding surface comes into contact with the insertion recession and the second sliding surface comes into contact with the first guide rail, the sliding member is pushed toward the screw hole such that the first sliding surface is inserted into the first guide rail, and the second sliding surface is inserted into the second guide rail, thereby allowing the sliding member to be seated in the accommodation space.

In the spine fixing apparatus according to the embodiment of the present invention, the sliding member may include a covering side for connecting a first end of the side wall, the first end being oriented toward the screw hole; and the covering side is formed to be curved in a shape that corresponds to an outer circumferential surface of the screw hole so as to avoid covering the screw hole in the unlock mode, whereby in the unlock mode, the sliding member is prevented from hindering insertion of the screw.

In the spine fixing apparatus according to the embodiment of the present invention, the rotation member may include a rotation main body, the rotation main body being in a rhombic shape and having a major axis perpendicular to the moving direction of the sliding members; and the sliding member may include a contact side for connecting a second end of the side wall, wherein the contact side is formed to be in a concave shape complementary to an outer circumferential surface of the rotation main body, thereby in the unlock mode, the contact side comes into contact with the outer circumferential surface of the rotation main body so as to surround the outer circumferential surface of the rotation main body.

In the spine fixing apparatus according to the embodiment of the present invention, when the rotation member rotates so as to be oriented to a direction that the major axis of the rotation main body is in parallel with the moving direction of the sliding members, the rotation member may push the sliding member such that the sliding member rectilinearly moves along the first guide rail and the second guide rail; the rectilinear motion of the sliding member toward the screw hole may be limited by the side ridges being locked to the locking corner, and each end of the major axis of the rotation main body may support a notch of the contact side so as to limit the rectilinear motion of the sliding member toward the rotation member, whereby the sliding member may be locked, covering a portion of the screw hole; and even when the screw pushes up the sliding member, the first guide rail may press the first sliding surface, and the second guide rail may press the second sliding surface, whereby the sliding member may not be separated from the accommodation space, thus preventing the screw from falling out by being loosed.

In the spine fixing apparatus according to the embodiment of the present invention, the plate may include a rotation member hole formed through the plate at a center of the rotation member, and the rotation member includes a rotation center for being received by the rotation member hole by protruding from a lower surface of the rotation main body; and the rotation center protruding from a lower surface of the plate is riveted so as to prevent the rotation member from being separated from the plate when the rotation member is coupled to the plate.

In the spine fixing apparatus according to the embodiment of the present invention, the rotation member may include a locking protrusion for pressing the lower surface of the accommodation space by protruding from the lower surface of the rotation main body; and the plate may include a locking groove for receiving the locking protrusion at a location where in the lock mode, the locking protrusion is seated, by being depressed from the lower surface of the accommodation space in a shape complementary to a shape of the locking protrusion.

In the spine fixing apparatus according to the embodiment of the present invention, the rotation center of the rotation member may be riveted, and the locking protrusion may generate friction by pressing the lower surface of the accommodation space, whereby the rotation member may not be easily rotated but rotated by a rotation tool having a groove, the groove being in a shape complementary to the outer circumferential surface of the rotation main body.

In the spine fixing apparatus according to the embodiment of the present invention, the pair of the screw holes may be spaced apart from another pair of the screw holes at predetermined intervals; and the plate may further include a window with a predetermined surface area, the window formed through a space between the pair of the screw holes and neighboring pair of the screw holes, wherein each pair of the screw holes is spaced apart from each other.

Advantageous Effects

According to the present invention having the above-described characteristics, it is possible to gain following advantage.

The spine fixing apparatus according to the present invention is advantageous in that the spine fixing apparatus is capable of easily switching between the lock mode and the unlock mode through simple mechanism by using screw holes, a rotation member for rotary motion at a predetermined location between the screw holes, and sliding members provided at opposite sides of the rotation member for rectilinear motion, thereby facilitating a surgical procedure.

Further, the spine fixing apparatus according to the present invention is advantageous in that the sliding member is seated in an accommodation space of a plate, whereby even when the screw pushes up the sliding member in the lock mode, the sliding member is not separated from the plate, thereby being capable of firmly locking the screw.

Further, the spine fixing apparatus according to the present invention is advantageous in that the rotation member is in a rhombic shape that has a major axis and a minor axis, thereby having smaller radius of gyration than that of rectangular shape. Thus, it is possible to reduce overall size of the apparatus, thereby enabling the plate to be bent easily.

Further, the spine fixing apparatus according to the present invention is advantageous in that in the lock mode, each end of the major axis of the rotation member supports a notch of a contact side, thereby stably supporting the sliding member. Thus, it is possible to limit the rectilinear motion of the sliding member efficiently.

Further, the spine fixing apparatus according to the present invention is advantageous in that undesirable rotation caused by the external environment can be prevented by friction generated when a locking protrusion of the rotation member presses the plate; and in the lock mode, the locking protrusion is seated on a locking groove of the plate, thereby preventing rotation of the rotation member and stably supporting the sliding member. Thus, it is possible to increase the success rate of an operation.

Further, the spine fixing apparatus according to the present invention is advantageous in that it is easy to perform a surgical procedure through a window that is penetrately formed through the plate by securing a clear view of the surgical region.

Furthermore, the spine fixing apparatus according to the present invention is advantageous in that it is easy to bend the plate corresponding to a cervical spine of a patient by providing a window in the plate.

BEST MODE

Reference will now be made in greater detail to an exemplary embodiment of the present invention, an example of which is illustrated in the accompanying drawings. Various modifications, additions and substitutions of the embodiment of the present invention are possible without departing from the scope and spirit of the invention, and thus it will be appreciated that the present invention is not limited to the following embodiment. The embodiment of the present invention has been disclosed for illustrative purposes for those skilled in the art. Accordingly, shapes of elements in drawings have been exaggerated for illustrative purposes.

A spine fixing apparatus according to the present invention is used to fix a spine that was damaged or deformed by external shock from an accident, or from long term bad posture. For example, the spine fixing apparatus may be applied to a cervical spine C. Reference will be made in detail to the present invention based on the cervical spine, hereinbelow.

Figure 1:
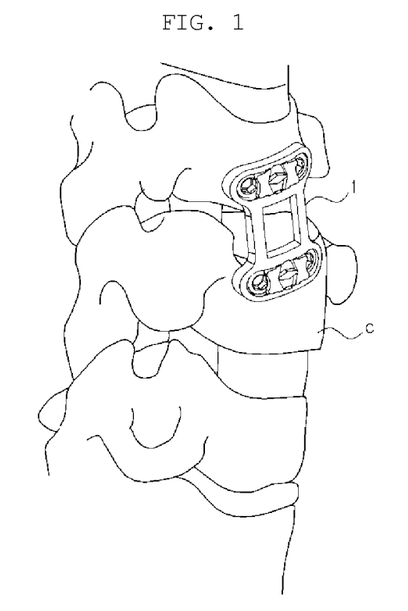
FIG. 1 is a referential view illustrating a state where a spine fixing apparatus according to the present invention is applied to cervical spine.
Figure 2:
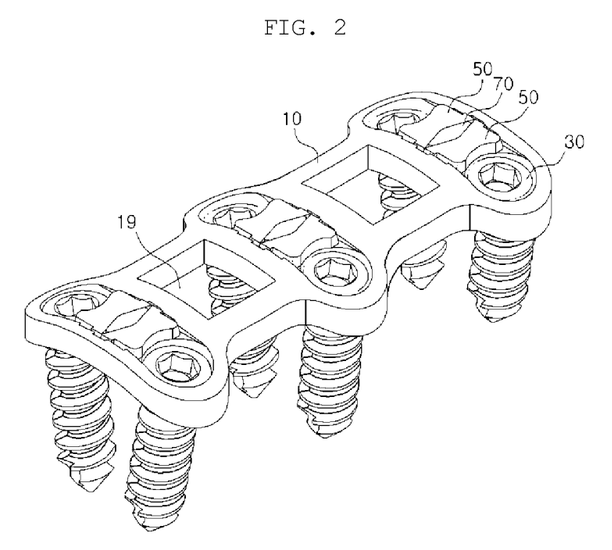
FIG. 2 is a perspective view illustrating an unlock mode of the spine fixing apparatus according to the present invention.
Figure 3:
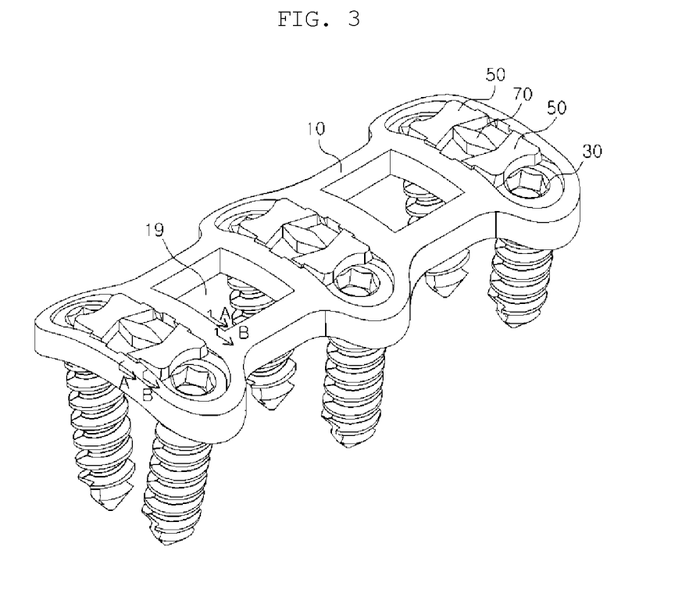
FIG. 3 is a perspective view illustrating a lock mode of the spine fixing apparatus according to the present invention.

With reference to FIGS. 1 to 14, the spine fixing apparatus 1 according to the present invention includes: a plate 10 fixed to a cervical spine C; screws 30 inserted into the cervical spine by being coupled to the plate 10; a rotation member 70 for rotary motion at a predetermined location between the screws 30; and sliding members 50 provided at opposite sides of the rotation member 70 for rectilinear motion, wherein the rotation member 70 and the sliding members 50 have symmetrical structures based on the rotation member 70. The spine fixing apparatus is capable of switching between lock and unlock modes, wherein as shown in FIG. 2, the unlock mode is a state where the sliding member 50 is prevented from hindering insertion of the screw 30 so as to allow the screw 30 being coupled to the plate 10 to be inserted into the cervical spine C; and as shown in FIG. 3, the lock mode is a state where the sliding member 50 covers a portion of an upper surface of the screw 30 that is inserted into both the plate 10 and the cervical spine, thereby preventing a back-out problem, which means the screw that is fixedly inserted into the cervical spine falls out by being loosed.

The plate 10 is for fixing the cervical spine C so as not to move, wherein the plate 10 fixedly connects between the cervical vertebrae to fix a damaged or deformed cervical spine C. The plate 10 is fixed to the cervical spine C by the screws 30.

Figure 4:
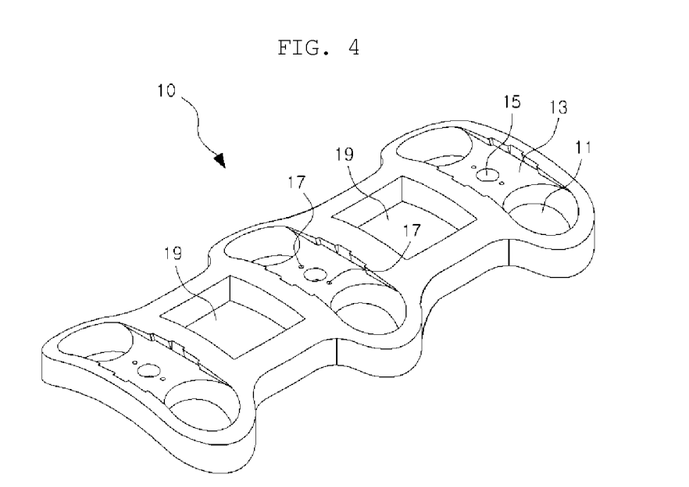
FIG. 4 is a perspective view illustrating a plate of FIG. 2.

As shown in FIG. 4, the plate 10 may include a plurality of screw holes 11 for allowing the screws 30 to be inserted thereinto by being formed through the plate 10. The number of the screw holes 11 may correspond to the number of the screws 30 that are used to fix the plate 10. Preferably, a pair of screw holes 11 may be formed through the plate 10 and each pair of screw holes 11 may be spaced apart from each other at predetermined intervals. The spine fixing apparatus 1 according to FIGS. 2 and 3 is configured such that three pairs of screw holes 11 are spaced apart from each other at predetermined intervals. However, as shown in FIG. 1, two pairs of screw holes 11 may be formed, or three or more pairs of screw holes 11 may be formed, depending on an operator's decision considering a surgical purpose, surgical region, surgical situation, etc.

The plate 10 may include a window 19 with a predetermined surface area, the window formed through a space between the pair of the screw holes 11 and neighboring pair of the screw holes 11, wherein each pair of the screw holes 11 is spaced apart from each other at predetermined intervals. The window 19 is in a predetermined shape. Preferably, the window 19 may be in a quadrilateral shape. An operator can identify a surgical region through the window 19 with his/her naked eye, thereby facilitating a surgical procedure. Further, the plate 10 is easily bent because of the window 19 formed therethrough, whereby an operator can bend the plate 10 into a suitable shape for a patient's cervical spine C, and can closely fix the plate 10 to the cervical spine C.

Figure 5:
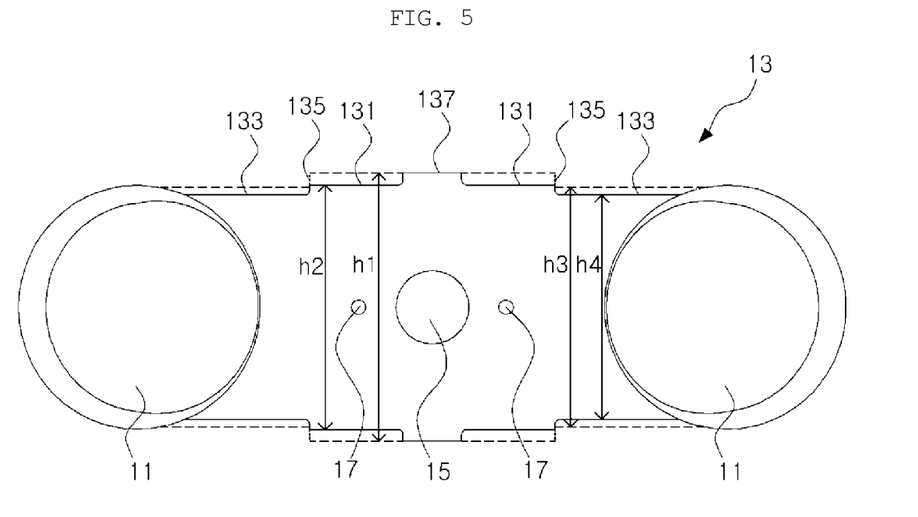
FIG. 5 is a plane view illustrating an accommodation space of FIG. 4.

As shown in FIG. 5, the plate 10 may include an accommodation space 13 formed on an upper surface thereof by being depressed in a moving direction of the sliding members 50 for accommodating the sliding members 50 and the rotation member 70 within the accommodation space 13; a rotation member hole 15 formed through a center of the accommodation space 13 for allowing the rotation member 70 to be inserted thereinto; and a locking groove 17 formed on a lower surface of the accommodation space 13 by being depressed in a shape complementary to a shape of a locking protrusion 75 of the rotation member 70, the locking protrusion 75 being described hereinbelow, for receiving the locking protrusion 75 in the lock mode.

The accommodation space 13 is formed on the upper surface of the plate 10 by being depressed so as to accommodate the sliding member 50 and the rotation member 70 and guide the rectilinear motion of the sliding member 50. The sliding member 50 has a depth corresponding to a thickness of the rotation member 70 such that the spine fixing apparatus 1 according to the present invention has an almost constant thickness even when the sliding member 50 and the rotation member 70 are mounted to the accommodation space 13.

The accommodation space 13 includes an upper portion that is open to outside; a lower surface that forms an outer surface of the plate 10 by being depressed on the plate 10; and a side surface that is in an inclined shape and connects the upper portion and the lower surface of the accommodation space 13.

An overall outline of the lower surface of the accommodation space 13 is two-stage rail shaped having respective widths of h1 and h3; and an overall outline of the upper portion of the accommodation space 13 is three-stage rail shaped having respective widths of h1, h2 and h4.

The side surface of the accommodation space 13 is in an inclined shape to have a progressively narrower gap between opposed sides thereof as approaching from the lower surface of the accommodation space 13 to the upper portion thereof, except for an insertion recession 137 that is described hereinbelow. The side surface of the accommodation space 13 includes a first guide rail 131, a second guide rail 133, a locking corner 135, and the insertion recession 137.

Figure 6:
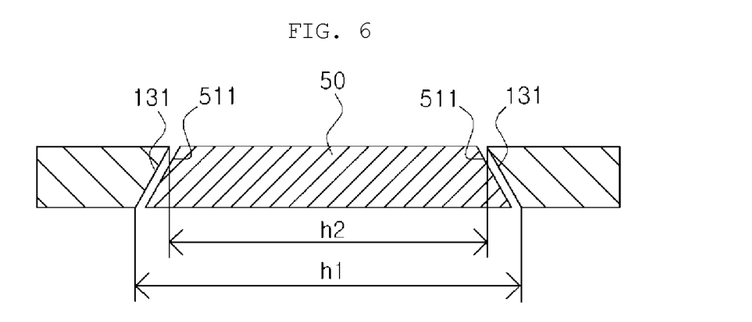
FIG. 6 is a sectional view taken along line A-A of FIG. 3.

The first guide rail 131 is for guiding the rectilinear motion of the sliding member 50 at a location where the accommodation space 13 comes into contact with the sliding member 50, wherein the first guide rail 131 is configured to have a sliding surface so as to have a progressively narrower gap between opposed sides thereof with respective widths of h1 at a lower surface thereof and h2 at an upper surface thereof. Thereby, as shown in FIG. 6, the first guide rail 131 presses the sliding member 50 so as to prevent the sliding member 50 from being separated from the accommodation space 13, and thus in the lock mode, even when the screw 30 pushes up the sliding member 50, the screw 30 is prevented from falling out by being loosed, namely preventing the back-out problem.

Figure 7:
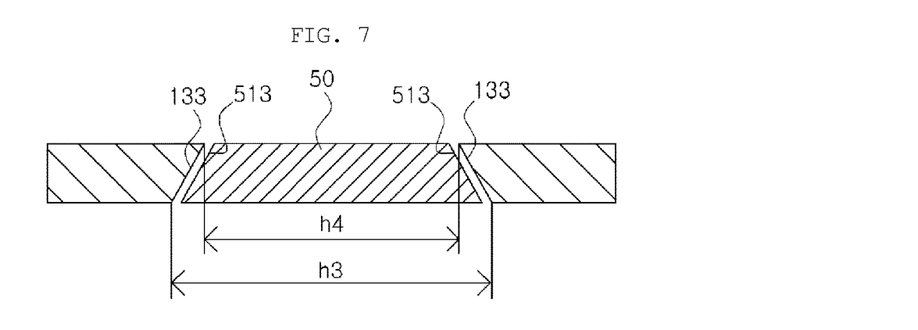
FIG. 7 is a sectional view taken along line B-B of FIG. 3.

The second guide rail 133 is for guiding the rectilinear motion of the sliding member 50 at a location where the accommodation space 13 comes into contact with the sliding member 50, wherein the second guide rail 133 is formed by extending from the first guide rail 131, having a sliding surface so as to have a progressively narrower gap between opposed sides thereof with respective widths of h3 at a lower surface thereof and h4 at an upper surface thereof. Thereby, as shown in FIG. 7, the second guide rail 133 presses the sliding member 50 so as to prevent the sliding member 50 from being separated from the accommodation space 13, and thus in the lock mode, even when the screw 30 pushes up the sliding member 50, the screw 30 is prevented from falling out by being loosed, namely preventing the back-out problem.

In the present invention, the first guide rail 131 and the second guide rail 133 may have widths capable of preventing the sliding member 50 from being separated from the accommodation space 13. Preferably, the widths of the first guide rail 131 and the second guide rail 133 may have an inequality relation of h1>h2>h3>h4 therebetween, so as to allow the sliding member 50 to pass through the insertion recession 137. Reference will be made in detail to the inequality relation, hereinafter.

The locking corner 135 is formed by being bent from the first guide rail 131 at almost right angle, so as to connect a first end of the first guide rail 131 with a first end of the second guide rail 133, wherein a side ridge 515 of the sliding member 50, which is described hereinbelow, is locked to the locking corner 135, thereby limiting the rectilinear motion of the sliding member 50. A detailed description thereof will be made, hereinafter.

The insertion recession 137 is used as a passage for inserting the sliding member 50 into the accommodation space 13, wherein the insertion recession 137 is formed at a center of the first guide rail 131 at right angle, has no sliding surface, and has a width of h1 from the lower surface of the accommodation space 13 to the upper portion thereof. Thereby, from a plane view, the insertion recession 137 is seemingly recessed from the first guide rail 131 toward an outside of the accommodation space 13.

Hereinbelow, with reference to FIG. 8, reference will be made to a process of inserting the sliding member 50 into the accommodation space 13 via the insertion recession 137.

Figure 8:
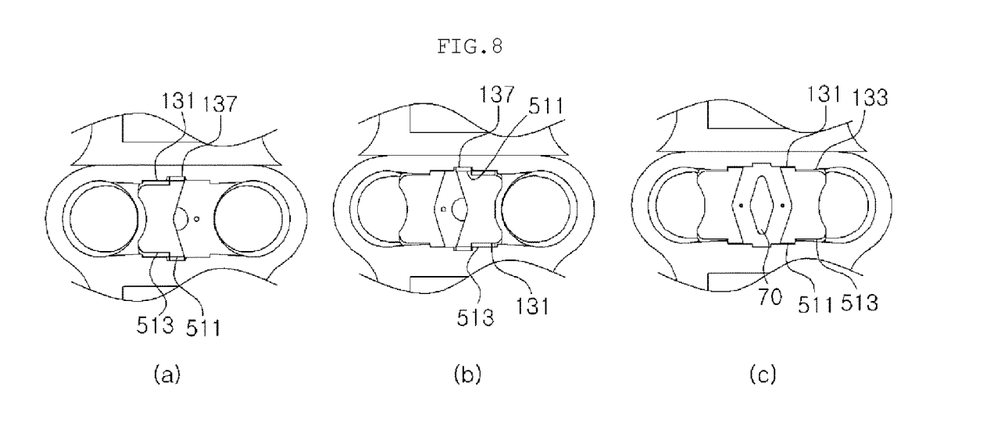
FIG. 8 is a referential view illustrating an assembly process of a sliding member and a rotation member.

As shown in FIG. 8(a), the sliding member 50 is inserted into the accommodation space 13 from the upper portion of the accommodation space 13 in a state where the first sliding surface 511 comes into contact with the insertion recession 137 and the second sliding surface 513 comes into contact with the first guide rail 131. Here, as shown in FIGS. 5 to 7, the insertion recession 137 has a width of h1 at the upper portion of the accommodation space 13; the first sliding surface 511 has a width of h1 at a lower surface of the sliding member 50; the first guide rail 131 has a width of h2 at the upper portion of the accommodation space 13; and the second sliding surface 513 has a width of h3 at the lower surface of the sliding member 50. As described above, in the accommodation space 13 having the inequality relation of h1>h2>h3>h4, the sliding member 50 can be inserted into the accommodation space 13 from the upper portion of the accommodation space 13.

And then, as shown in FIG. 8(b), after the sliding member 50 is inserted into the accommodation space 13 in a state where the first sliding surface 511 comes into contact with the first guide rail 131 and the second sliding surface 513 comes into contact with the second guide rail 133, an opposite sliding member 50 is inserted into the accommodation space 13 in a same manner described above.

After the sliding members 50 are inserted into the accommodation space 13, as shown in FIG. 8(c), the rotation member 70 is coupled to the accommodation space 13, thereby preventing the sliding members 50 from being separated from the accommodation space 13 via the insertion recession 137.

As shown in FIGS. 4 and 5, the locking groove 17 is formed at a location where in the lock mode, a locking protrusion 75 described hereinafter is seated, by being depressed from the lower surface of the accommodation space 13 in a shape complementary to a shape of the locking protrusion 75 so as to receive the locking protrusion 75. Reference will be made in detail to the locking groove, hereinafter.

Figure 9:
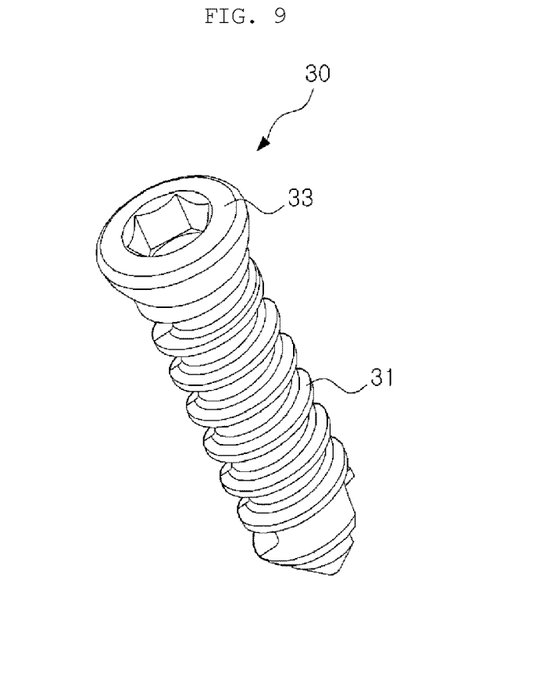
FIG. 9 is a perspective view illustrating a screw of FIG. 2.

As shown in FIG. 9, the screw 30 is fixedly inserted into the cervical spine C directly, so as to fix the plate 10 to the cervical spine C. The screw 30 includes a screw main body 31 having male threads and female threads on an outer circumferential surface thereof for being inserted into the cervical spine C; and a head 33 provided at an upper portion of the screw main body 31 in a crown shape for being seated in the screw hole 11.

Figure 10:
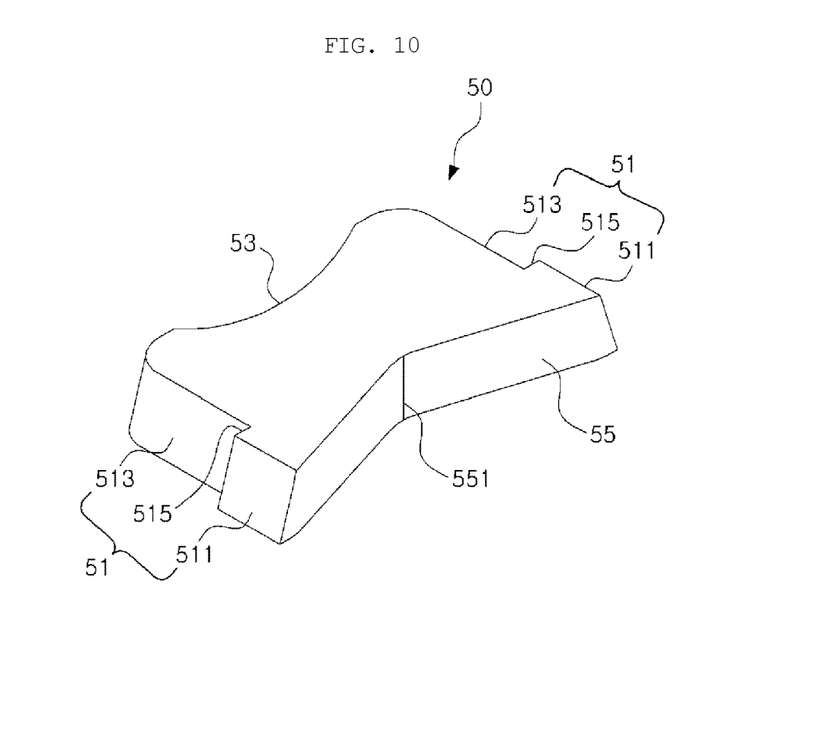
FIG. 10 is a perspective view illustrating the sliding member of FIG. 2.

As shown in FIG. 10, the rectilinear motion of the sliding member 50 is guided by both the first guide rail 131 and the second guide rail 133 in a state where the sliding member 50 is mounted within the accommodation space 13. In the unlock mode, the sliding member 50 uncovers the screw hole 11; on the contrary, in the lock mode, the sliding member 50 covers a portion of the screw hole 11, thereby preventing the back-out problem. The sliding member 50 includes a side wall 51, a covering side 53, and a contact side 55.

The side wall 51 is a portion that comes into contact with both the first guide rail 131 and the second guide rail 133, wherein the side wall 51 includes a first sliding surface 511, a second sliding surface 513, and a side ridge 515, forming a side surface of the sliding member 50.

As shown in FIG. 6, the first sliding surface 511 is in an inclined shape complementary to a shape of the first guide rail 131 so as to come into contact with the first guide rail 131. As shown in FIG. 7, the second sliding surface 513 is in an inclined shape complementary to a shape of the second guide rail 133 so as to come into contact with the second guide rail 133. Thus, the first guide rail 131 presses the first sliding surface 511, and the second guide rail 133 presses the second sliding surface 513, thereby preventing the sliding member 50 from being separated from the accommodation space 13.

The side ridge 515 is formed by being bent and extending from a first end of the first sliding surface 511 to an inside of the sliding member 50 at almost right angle, wherein the side ridge 515 limits the rectilinear motion of the sliding member 50 by coming into contact with the locking corner 135. A detailed description thereof will be made, hereinafter.

The covering side 53 is for connecting a second end of the second sliding surface 513. When the sliding member 50 is inserted into the accommodation space 13, the covering side 53 is oriented toward the screw hole 11. The covering side 53 is configured to be curved in a shape that corresponds to a hemispherical shape of the screw hole 11 so as to avoid covering the screw hole 11, in the unlock mode. Thus, in the unlock mode, the screw 30 can be inserted into the screw hole 11 with no hindrance of the sliding member 50. Further, it is possible to reduce an overall size of the apparatus because a range of the rectilinear motion of the sliding member 50 with the curved covering side 53 is narrower than the range with a straight covering side.

The contact side 55 is for connecting a second end of the first sliding surface 511. When the sliding member 50 is inserted into the accommodation space 13, the contact side 55 is oriented toward the rotation member 70. The contact side 55 is in a shape complementary to a shape of the rotation member 70, thereby forming a notch 551, which is described hereinbelow. Thus, the sliding member 50 is disposed near the center of the accommodation space 13 by coming into as close of contact with the rotation member 70 as possible, so that the screw 30 can be inserted into the screw hole 11 with no hindrance of the sliding member 50.

Figure 11:
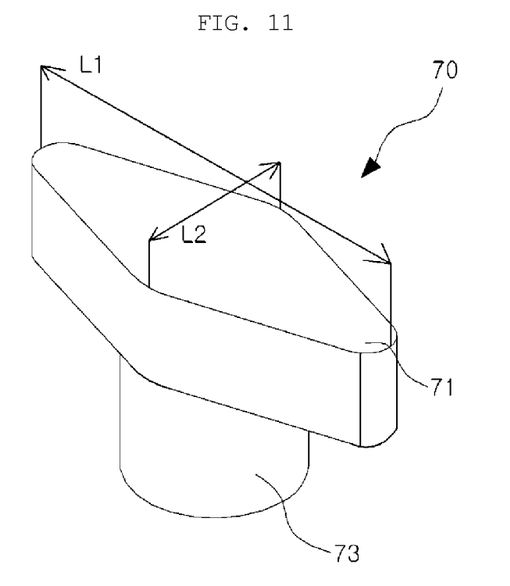
FIG. 11 is a top perspective view illustrating the rotation member of FIG. 2.
Figure 12:
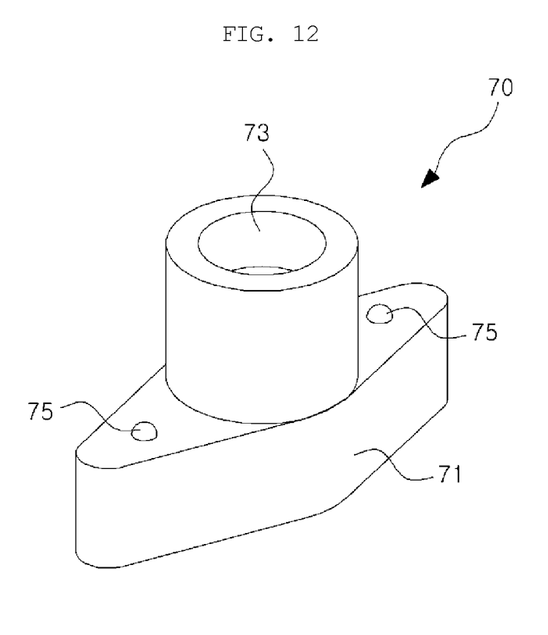
FIG. 12 is a perspective view illustrating a lower surface of the rotation member of FIG. 2.

As shown in FIGS. 11 and 12, the rotation member 70 is inserted into the rotation member hole 15, and thereby rotatably moves at the center of the accommodation space 13. Thus, in the unlock mode, the rotation member 70 prevents the sliding member 50 from being separated from the accommodation space 13 via the insertion recession 137; and in the lock mode, the rotation member 70 pushes the sliding member 50 toward the screw hole 11 to rectilinearly move so that the sliding member 50 can be locked, covering the screw hole 11. The rotation member 70 includes a rotation main body 71, a rotation center 73, and a locking protrusion 75.

The rotation main body 71 is for rotatably moving within the accommodation space 13 and is in a rhombic shape having a major axis L1 and a minor axis L2. Thus, the contact side 55 is configured to have the notch 551 so as to come into close contact with an outer circumferential surface of the rotation main body 71.

Figure 13:
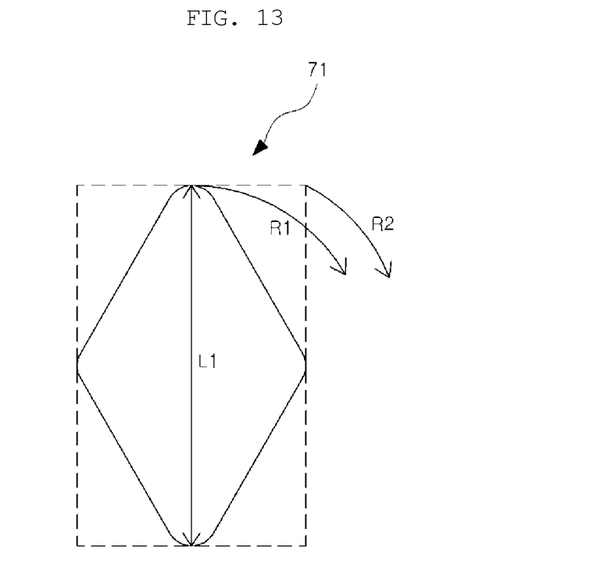
FIG. 13 is a referential view illustrating radius of gyration of the rotation member of FIG. 2.

As shown in FIG. 13, the rotation main body 71 is in a rhombic shape, thereby having smaller radius of gyration R1 than radius of gyration of a rectangular shape, during the rotary motion with a same major axis L1. Thus, it is possible to reduce an overall size of the apparatus. Further, as described hereinbelow, in the lock mode, each end of the major axis L1 supports the notch 551 of the contact side 55, thereby being capable of stably locking the sliding member 50.

The rotation center 73 is formed by protruding from a lower surface of the rotation main body 71 so that the rotation member 70 can be coupled to the plate 10 by being inserted into the rotation member hole 15. The rotation center 73 has a protruding length capable of a bit protruding from a lower surface of the plate 10. After the rotation member 70 is coupled to the plate 10, the rotation center 73 is riveted and pressed, thereby firmly locking the rotation member 70 so as to prevent the rotation member 70 from being rotated by hand. Thus, it is possible to prevent the rotation member 70 from being rotated (loosened) by the external environment after surgical procedure.

The locking protrusion 75 is formed to be in a predetermined shape by protruding from the lower surface of the rotation main body 71. When the rotation member 70 rotatably moves, the locking protrusion 75 presses the lower surface of the accommodation space 13, thereby firmly locking the rotation member 70 so as to prevent the rotation member 70 from being rotated by hand. Further, in the lock mode, the locking protrusion 75 is seated on the locking groove 17, whereby the rotation member 70 is locked at a location where the rotation member 70 supports the sliding member 50, preventing the rotation member 70 from being rotated (loosened) by the external environment, in cooperation with a riveting pressure.

The locking protrusion 75 and the locking groove 17 may be in predetermined shapes. Preferably, the locking protrusion 75 and the locking groove 17 may be in hemispherical shapes complementary to each other so that the locking protrusion 75 can be received in the locking groove 17. Further, preferably, the locking protrusions 75 may be provided on opposite sides of the major axis of the rotation main body 71, respectively, wherein the rotation center 73 is between the locking protrusions 75; and the locking groove 17 may be formed by being depressed at a location where in the lock mode, the locking protrusion 75 is seated.

The rotation member 70 cannot be rotated by hand because of both the riveting pressure of the rotation center 73 and a pressure of the locking protrusion 75, whereby the rotation member 70 can be rotated by a rotation tool 77 having a groove that is in a shape complementary to a shape of the rotation main body 71. A detailed description thereof will be made, hereinafter.

Hereinbelow, with reference to FIGS. 8 and 14, reference will be made in detail to use of the spine fixing apparatus 1 during surgical procedure.

As shown in FIGS. 8(a) and 8(b), after the sliding member 50 is inserted into the accommodation space 13 via the insertion recession 137, the rotation member 70 is inserted into the rotation member hole 15. And then, the sliding member 50 and the rotation member 70 are coupled to the plate 10 by being riveted on the lower surface of the plate 10.

Figure 14:
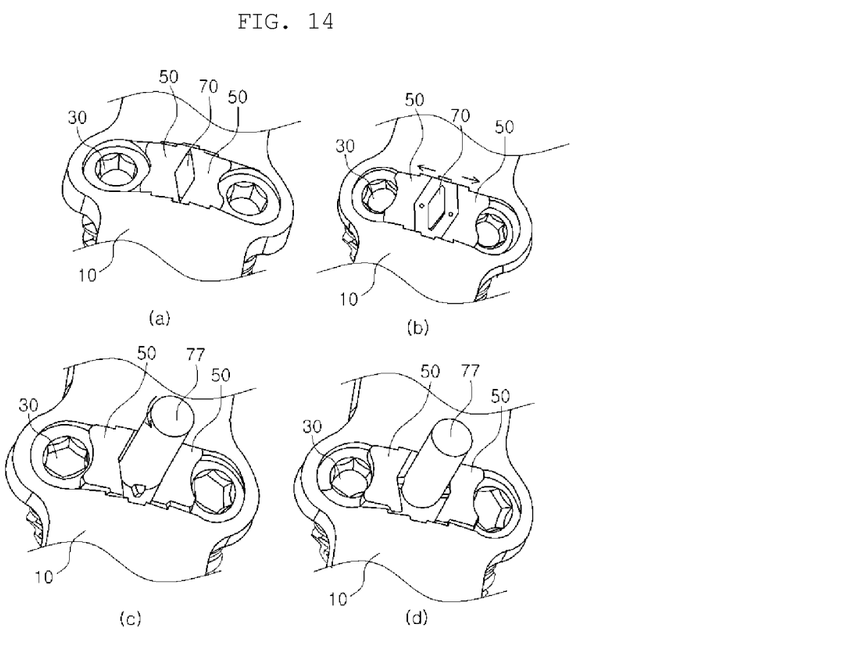
FIG. 14 is a referential view illustrating a process of switching from the unlock mode to the lock mode of the spine fixing apparatus according to the present invention.

As shown in FIG. 14(a), after the sliding member 50 is rectilinearly moved to come into close contact with the rotation member 70 so as not to cover the screw hole 11, the screw 30 is inserted into the screw hole 11 in a state where the plate 10 is attached to the cervical spine C, to which the plate 10 is fixed, thereby fixing the plate 10 to the cervical spine C. The covering side 53 is in a shape corresponding to an outline of the outer circumferential surface of the screw hole 11; and the contact side 55 is in a shape complementary to the outer circumferential surface of the rotation main body 71, whereby the sliding member 50 can be disposed as near to the center of the accommodation space 13 as possible. Thus, it is possible to insert the screw 30 into the screw hole with no hindrance of the sliding member 50.

As shown in FIG. 14(b), in order to secure room for coupling the rotation member 70 with the rotation tool 77, the sliding member 50 is rectilinearly moved toward the screw hole 11, to a predetermined distance. However, in the case when room for coupling the rotation member 70 with the rotation tool 77 is not required depending on a type or a shape of the rotation tool 77, this step can be skipped.

As shown in FIG. 14(c), after the groove of the rotation tool 77 is inserted into the rotation main body 71, the rotation tool 77 is rotated such that the major axis L1 of the rotation main body 71 is in parallel with the moving direction of the sliding members 50. As the rotation member 70 rotates, the sliding member 50 is pushed by the rotation member 70, thereby rectilinearly moving within the accommodation space 13 along the first guide rail 131 and the second guide rail 133.

As shown in FIG. 14(d), the side ridge 515 comes into close contact with the locking corner 135, thereby limiting the rectilinear motion of the sliding member 50 toward the screw hole 11. Further, each end of the major axis L1 of the rotation main body 71 supports the notch 551 of the contact side 55, whereby the sliding member 50 is locked, covering the portion of the screw hole 11. Furthermore, the side wall 51 of the sliding member 50 is pressed by both the first guide rail 131 and the second guide rail 133, thereby preventing the sliding member 50 from being separated from the accommodation space 13. Thus, it is possible to prevent the back-out problem.

As described above, the spine fixing apparatus 1 according to the present invention is capable of easily switching between the lock mode and the unlock mode through mechanism of coupling locations, shapes, and the rectilinear motion and rotary motion of the sliding member 50 and the rotation member 70, and is capable of preventing the back-out problem, efficiently.

Further, the spine fixing apparatus according to the present invention is provided with the window 19 in the plate 10, thereby enabling an operator to identify the surgical region with his/her naked eye, thus facilitating a surgical procedure. In addition, the window 19 enables an operator to easily bend the plate 10 into a suitable shape for a patient's cervical spine C, and closely fix the plate 10 to the cervical spine C.

The detailed description above is an example of the present invention. Accordingly, the present invention can be used all over the spine, and it will be appreciated that the present invention is not limited to the cervical spine. Although the preferred embodiment of the present invention has been disclosed for illustrative purposes, it will be appreciated that the present invention is not limited thereto, and can be used under various combinations, modifications and situations. In other words, various modifications, additions and substitutions are possible, without departing from the scope and spirit of the invention. Although the embodiment mentioned above is for explaining best mode for realizing spirit of the present invention, the present invention, various modifications are possible for specific applications and uses. Thus, the detailed description of the present invention, as disclosed embodiment, does not intend to limit the present invention. Further, it will be appreciated that the accompanying claims include other embodiments.

The invention claimed is:

1. A spine fixing apparatus, comprising:
a plate fixable to a spine;
screws insertable into the spine by being coupled to the plate;
a rotation member for rotary motion at a predetermined location between the screws; and
sliding members provided at opposite sides of the rotation member for rectilinear motion, wherein each of the sliding members is disposed between the rotation member and each of the screws, wherein
the spine fixing apparatus is capable of switching between a lock mode and an unlock mode.

2. The spine fixing apparatus of claim 1, wherein
the plate includes a plurality of screw holes for allowing the screws to be inserted thereinto, the screw holes being spaced apart from each other at predetermined intervals on the plate and formed through the plate; and
the rotation member and the sliding members are disposed between a pair of the screw holes and the sliding members have symmetrical structures based on the rotation member.

3. The spine fixing apparatus of claim 2, wherein the plate includes an accommodation space formed by being depressed in a moving direction of the sliding members for accommodating the sliding members and the rotation member such that the sliding member rectilinearly moves within the accommodation space, and switches between the lock mode and the unlock mode.

4. The spine fixing apparatus of claim 3, wherein
the accommodation space includes a first guide rail for guiding a motion of the sliding member by being configured to have a sliding surface so as to have a progressively narrower gap between opposed sides of the first guide rail with which the sliding members come into contact, as approaching from a lower surface of the accommodation space to an upper surface thereof; and
a side wall of the sliding member comes into contact with the first guide rail, and includes a first sliding surface being in an inclined shape complementary to a shape of the first guide rail, wherein
the first guide rail presses the first sliding surface so as to prevent the sliding member from being separated from the accommodation space.

5. The spine fixing apparatus of claim 4, wherein
the accommodation space includes a locking corner formed by being bent from a first end of the first guide rail to an inside of the accommodation space at almost right angle, the first end being oriented toward the screw hole, and a second guide rail being in an inclined shape in a same manner of the first guide rail by extending from the locking corner toward the screw hole in parallel with the first guide rail; and
the side wall of the sliding member includes a side ridge formed by being bent from a first end of the first sliding surface to an inside of the sliding member at almost right angle, and a second sliding surface formed by being bent and extending from an end of the side ridge in parallel with the first sliding surface, and being in an inclined shape complementary to a shape of the second guide rail, wherein when switching to the lock mode, the side ridge is locked to the locking corner so as to limit the rectilinear motion of the sliding member, and the second guide rail presses the second sliding surface so as to prevent the sliding member from being separated from the accommodation space.

6. The spine fixing apparatus of claim 5, wherein
the accommodation space includes an insertion recession formed by being recessed from a second end of the first guide rail toward an outside of the accommodation space, the insertion recession being formed to have a width capable of receiving the first sliding surface of the sliding member, wherein
after the sliding member is inserted into the accommodation space from an upper portion of the accommodation space in a state where the first sliding surface comes into contact with the insertion recession and the second sliding surface comes into contact with the first guide rail, the sliding member is pushed toward the screw hole such that the first sliding surface is inserted into the first guide rail, and the second sliding surface is inserted into the second guide rail, thereby allowing the sliding member to be seated in the accommodation space.

7. The spine fixing apparatus of claim 6, wherein
the sliding member includes a covering side for connecting a first end of the side wall, the first end being oriented toward the screw hole; and the covering side is formed to be curved in a shape that corresponds to an outer circumferential surface of the screw hole so as to avoid covering the screw hole in the unlock mode, whereby
in the unlock mode, the sliding member is prevented from hindering insertion of the screw.

8. The spine fixing apparatus of claim 7, wherein
the rotation member includes a rotation main body, the rotation main body being in a rhombic shape and having a major axis perpendicular to the moving direction of the sliding members; and
the sliding member includes a contact side for connecting a second end of the side wall, wherein the contact side is formed to be in a concave shape complementary to an outer circumferential surface of the rotation main body, whereby
in the unlock mode, the contact side comes into contact with the outer circumferential surface of the rotation main body so as to surround the outer circumferential surface of the rotation main body.

9. The spine fixing apparatus of claim 8, wherein
when the rotation member rotates so as to be oriented to a direction that the major axis of the rotation main body is in parallel with the moving direction of the sliding members, the rotation member pushes the sliding member such that the sliding member rectilinearly moves along the first guide rail and the second guide rail;
the rectilinear motion of the sliding member toward the screw hole is limited by the side ridges being locked to the locking corner, and each end of the major axis of the rotation main body supports a notch of the contact side so as to limit the rectilinear motion of the sliding member toward the rotation member, whereby the sliding member is locked, covering a portion of the screw hole; and
even when the screw pushes up the sliding member, the first guide rail presses the first sliding surface, and the second guide rail presses the second sliding surface, whereby the sliding member is not separated from the accommodation space, thus preventing the screw from falling out by being loosed.

10. The spine fixing apparatus of claim 9, wherein
the plate includes a rotation member hole formed through the plate at a center of the rotation member, and the rotation member includes a rotation center for being received by the rotation member hole by protruding from a lower surface of the rotation main body; and
the rotation center protruding from a lower surface of the plate is riveted so as to prevent the rotation member from being separated from the plate when the rotation member is coupled to the plate.

11. The spine fixing apparatus of claim 10, wherein
the rotation member includes a locking protrusion for pressing the lower surface of the accommodation space by protruding from the lower surface of the rotation main body; and
the plate includes a locking groove for receiving the locking protrusion at a location where in the lock mode, the locking protrusion is seated, by being depressed from the lower surface of the accommodation space in a shape complementary to a shape of the locking protrusion.

12. The spine fixing apparatus of claim 11, wherein
the rotation center of the rotation member is riveted, and the locking protrusion generates friction by pressing the lower surface of the accommodation space, whereby the rotation member is not easily rotated but rotated by a rotation tool having a groove, the groove being in a shape complementary to an outer circumferential surface of the rotation main body.

13. The spine fixing apparatus of claim 2, wherein
the pair of the screw holes are spaced apart from another pair of the screw holes at predetermined intervals; and
the plate further includes a window with a predetermined surface area, the window formed through a space between the pair of the screw holes and neighboring pair of the screw holes, wherein each pair of the screw holes is spaced apart from each other.

* * * * *